US009566140B2

(12) United States Patent
Brown et al.

(10) Patent No.: US 9,566,140 B2
(45) Date of Patent: Feb. 14, 2017

(54) METHOD AND DEVICE FOR WHITENING TEETH USING SONOCHEMISTRY

(75) Inventors: Damon Brown, Boston, MA (US); Mark Edward Farrell, Medfield, MA (US); Arshad Ali, Toronto (CA); Tim Diasti, Clearwater, FL (US); Graham K. Philp, Jr., Naples, FL (US); Graham K. Parrish-Philp, legal representative, San Diego, CA (US); David Wuchinich, Yonkers, NY (US)

(73) Assignee: Dentovations Inc., Boston, MA (US)

( * ) Notice: Subject to any disclaimer, the term of this patent is extended or adjusted under 35 U.S.C. 154(b) by 0 days.

(21) Appl. No.: 13/341,093

(22) Filed: Dec. 30, 2011

(65) Prior Publication Data

US 2013/0004912 A1 Jan. 3, 2013

Related U.S. Application Data

(63) Continuation-in-part of application No. 12/585,215, filed on Sep. 8, 2009, now abandoned, which is a
(Continued)

(51) Int. Cl.
| | | |
|---|---|---|
| *A61C 15/00* | (2006.01) | |
| *A61C 17/20* | (2006.01) | |
| *A61C 19/06* | (2006.01) | |

(52) U.S. Cl.
CPC .............. *A61C 17/20* (2013.01); *A61C 19/06* (2013.01); *A61C 19/066* (2013.01)

(58) Field of Classification Search
CPC ........ A61C 19/06; A61C 19/066; A61C 17/20
(Continued)

(56) References Cited

U.S. PATENT DOCUMENTS 3,278,520 A 10/1966 Klug
3,278,521 A 10/1966 Klug
(Continued)

FOREIGN PATENT DOCUMENTS

EP 0 539 315 A2 4/1993
WO WO 9940870 A1 2/1999
(Continued)

OTHER PUBLICATIONS

U.S. Appl. No. 61/428,804, filed Dec. 2010, Brown et al.
(Continued)

*Primary Examiner* — Heidi M Eide
(74) *Attorney, Agent, or Firm* — Shlesinger, Arkwright & Garvey LLP (57) ABSTRACT

Tooth whitening device for whitening teeth using sonochemistry includes a body, and an ultrasonic transducer provided in the body. The ultrasonic transducer is configured for producing ultrasonic waves in the range of 20-100 kHz, and good results have been achieved with ultrasonic waves at a frequency of 40 kHz. There is an ultrasonic horn provided on the body, and the ultrasonic horn is operatively connected with the ultrasonic transducer. A liquid retaining element is provided on the ultrasonic horn, and the liquid retaining element is configured for retaining a liquid tooth whitening composition against a user's teeth. The liquid retaining element may be a sponge or a replaceable pad, such as a foam pad.

17 Claims, 5 Drawing Sheets

Related U.S. Application Data continuation-in-part of application No. 11/412,076, filed on Apr. 27, 2006, now abandoned.

(60) Provisional application No. 60/675,089, filed on Apr. 27, 2005, provisional application No. 61/428,804, filed on Dec. 30, 2010.

(58) Field of Classification Search
USPC ......... 433/118–119, 215–216, 32, 86, 36, 37
See application file for complete search history.

(56) References Cited

U.S. PATENT DOCUMENTS

| | | | |
|---|---|---|---|
| 3,567,823 A | 3/1971 | Yamaga et al. | |
| 4,450,139 A | 5/1984 | Bussiere et al. | |
| 4,556,561 A | 12/1985 | Brown et al. | |
| 4,661,070 A | 4/1987 | Frieman | |
| 4,684,517 A | 8/1987 | Clipper et al. | |
| 4,952,143 A | 8/1990 | Becker et al. | |
| 4,976,955 A | 12/1990 | Libin | |
| 4,980,152 A | 12/1990 | Frazier et al. | |
| 4,983,380 A | 1/1991 | Yarborough | |
| 5,000,942 A | 3/1991 | Libin | |
| 5,008,582 A | 4/1991 | Tanuma et al. | |
| 5,032,178 A | 7/1991 | Cornell | |
| 5,084,268 A | 1/1992 | Thaler | |
| 5,139,768 A | 8/1992 | Friedman | |
| 5,171,564 A | 12/1992 | Nathoo et al. | |
| 5,208,010 A | 5/1993 | Thaler | |
| 5,217,710 A | 6/1993 | Williams et al. | |
| 5,234,342 A | 8/1993 | Fischer | |
| 5,264,205 A | 11/1993 | Kelly | |
| 5,279,816 A | 1/1994 | Church et al. | |
| 5,290,566 A | 3/1994 | Schow et al. | |
| 5,302,375 A | 4/1994 | Viscio | |
| 5,310,563 A | 5/1994 | Curtis et al. | |
| 5,372,802 A | 12/1994 | Barrows et al. | |
| 5,376,006 A | 12/1994 | Fischer | |
| 5,395,241 A | 3/1995 | Kandelman | |
| 5,403,577 A | 4/1995 | Friedman | |
| 5,403,578 A | 4/1995 | Gordon | |
| 5,409,631 A | 4/1995 | Fischer | |
| 5,425,953 A | 6/1995 | Sintov et al. | |
| 5,437,858 A | 8/1995 | Hungerbrach et al. | |
| 5,457,611 A | 10/1995 | Verderber | |
| 5,614,174 A | 3/1997 | Hsu et al. | |
| 5,631,000 A | 5/1997 | Pellico et al. | |
| 5,636,988 A | 6/1997 | Murayama | |
| 5,645,428 A | 7/1997 | Yarborough | |
| 5,690,912 A | 11/1997 | Campbell et al. | |
| 5,693,315 A | 12/1997 | Bevilacqua | |
| 5,698,182 A | 12/1997 | Prencipe et al. | |
| 5,708,052 A | 1/1998 | Fischer et al. | |
| 5,718,886 A | 2/1998 | Pellico | |
| 5,746,598 A | 5/1998 | Fischer | |
| 5,766,574 A | 6/1998 | Christina-Beck et al. | |
| 5,780,015 A | 7/1998 | Fisher et al. | |
| 5,785,527 A | 7/1998 | Jensen et al. | |
| 5,785,957 A | 7/1998 | Losee et al. | |
| 5,792,446 A | 8/1998 | Ashley | |
| 5,797,749 A | 8/1998 | Bertolotti et al. | |
| 5,814,304 A | 9/1998 | Wong et al. | |
| 5,820,852 A | 10/1998 | Burgess et al. | |
| 5,824,289 A | 10/1998 | Stoltz | |
| 5,846,570 A | 12/1998 | Barrow et al. | |
| 5,849,266 A | 12/1998 | Friedman | |
| 5,849,269 A | 12/1998 | Burgess et al. | |
| 5,851,512 A | 12/1998 | Fischer | |
| 5,855,870 A | 1/1999 | Fischer | |
| 5,858,332 A | 1/1999 | Jensen et al. | |
| 5,879,691 A | 3/1999 | Sagel et al. | |
| 5,891,453 A | 4/1999 | Sagel et al. | |
| 5,902,568 A | 5/1999 | Ryles et al. | |
| 5,928,628 A | 7/1999 | Pellico | |
| 5,985,249 A | 11/1999 | Fischer | |
| 6,030,222 A | 2/2000 | Tarver | |
| 6,036,493 A | 3/2000 | Sharma | |
| 6,095,813 A * | 8/2000 | Broyles | 433/80 |
| 6,102,696 A | 8/2000 | Osterwalder | |
| 6,183,251 B1 | 2/2001 | Fischer | |
| 6,312,666 B1 | 11/2001 | Oxman et al. | |
| 6,331,111 B1 | 12/2001 | Cao | |
| 6,343,933 B1 | 2/2002 | Montgomery | |
| 6,419,906 B1 | 7/2002 | Xu et al. | |
| 6,439,888 B1 | 8/2002 | Boutoussov et al. | |
| 6,517,350 B2 | 2/2003 | Diasti et al. | |
| 6,648,641 B1 | 11/2003 | Viltro et al. | |
| 6,770,266 B2 | 8/2004 | Santarpia, III et al. | |
| 6,902,398 B1 * | 6/2005 | Segal | 433/38 |
| 7,011,523 B2 | 3/2006 | Allred et al. | |
| 7,572,124 B2 | 8/2009 | Cipolla et al. | |
| 7,748,070 B2 | 7/2010 | Chan et al. | |
| 7,887,328 B2 | 2/2011 | Brown et al. | |
| 8,308,479 B2 | 11/2012 | Philp, Jr., et al. | |
| 2001/0046652 A1 | 11/2001 | Ostler et al. | |
| 2002/0004190 A1 | 1/2002 | Diasti et al. | |
| 2002/0047222 A1 | 4/2002 | Philp | |
| 2002/0064753 A1 | 5/2002 | Philp | |
| 2002/0106607 A1 * | 8/2002 | Horowitz | 433/118 |
| 2002/0177099 A1 | 11/2002 | Cao | |
| 2002/0179124 A1 * | 12/2002 | Van Hauwermeiren | A47L 13/00 134/34 |
| 2003/0017435 A1 | 1/2003 | Ibsen et al. | |
| 2003/0036037 A1 | 2/2003 | Zavitsanos et al. | |
| 2003/0091954 A1 | 5/2003 | West et al. | |
| 2005/0074723 A1 | 4/2005 | Ostler et al. | |
| 2005/0192348 A1 | 9/2005 | Bar-Or et al. | |
| 2005/0255054 A1 | 11/2005 | Philp et al. | |
| 2005/0260142 A1 | 11/2005 | Philp et al. | |
| 2006/0019220 A1 | 1/2006 | Loebel | |
| 2006/0141422 A1 | 6/2006 | Philp et al. | |
| 2006/0141423 A1 | 6/2006 | Brown et al. | |
| 2007/0009857 A1 | 1/2007 | Philp et al. | |
| 2007/0223988 A1 | 9/2007 | Gruenbacher et al. | |
| 2008/0293009 A1 | 11/2008 | Winston | |
| 2008/0311545 A1 | 12/2008 | Ostler | |
| 2009/0092643 A1 * | 4/2009 | De Vreese et al. | 424/401 |
| 2009/0148815 A1 | 6/2009 | Philp et al. | |
| 2009/0155740 A1 * | 6/2009 | Jensen et al. | 433/119 |
| 2009/0159089 A1 * | 6/2009 | Jansheski | 128/861 |
| 2009/0191510 A1 | 7/2009 | Larsen | |
| 2009/0325129 A1 | 12/2009 | Brown et al. | |

FOREIGN PATENT DOCUMENTS

| | | |
|---|---|---|
| WO | WO 01/26576 A1 | 10/2000 |
| WO | 2005/107638 | 11/2005 |
| WO | WO 2005/107638 A1 | 11/2005 |

OTHER PUBLICATIONS

Goldstein et al., eds., Complete Dental Bleaching, Ch. 4, Quintessence Publishing Co., Inc., Chicago (1995).
The Dental Advisor Plus, vol. No. 1, (Jan./Feb. 1996).
C. G. Toh, "Clinical Evaluation of a dual-activated bleaching system"; Asian J. Aesthet. Dent, I: 65-70, (1993).
PCT International Search Report in PCT/US11/68141, dated Jun. 12, 2012 (2 pgs.).
PCT Written Opinion of International Searching Authority in PCT/US11/68141, dated Jun. 12, 2012 (4 pgs.).
U.S. Appl. No. 12/585,215, filed Sep. 2009, Brown et al.
Union Broach Operator's Manual, "Operating Instructions Illuminator," Union Broach, A Health-Chem Company, pp. 1-15, cited in U.S. Pat. No. 6,162,055 before Dec. 2000.
QuasarBrite.TM., Contrast A.M..RTM., Laser Whitening Gel, Instructions for Use Manual, Interdent, Inc. (Los Angeles, CA), cited in U.S. Pat. No. 6,162,055 before Dec. 2000.
Shofu.RTM., HiLite.RTM. Dual Activated Bleaching System, Instruction Manual, Shofu Dental Corporation (Menlo Park, CA), Nov. 1997, cited in U.S. Pat. No. 6,162,055 before Dec. 2000.

(56) References Cited

OTHER PUBLICATIONS

Notification Concerning Transmittal and an International Preliminary Report on Patentability (IPRP) dated Oct. 22, 2013 (6 pages).
Replacement Sheets filed Nov. 17, 2010 in prosecution history of US2009/0155740 Jensen et al.
Applicant Comments of Oct. 2, 2014 marked on Fig. 4A of US2009/0155740 Jensen et al. as filed (1 p.).
Van Randeraat, J. et al., Piezoelectric Ceramics, N. V.Philips Gloeilampenfabrieken, Eindhoven, Netherlands (NL),$2^{nd}$ Ed., Jan. 1974, part 4 "PXE Flexure Elements", pp. 40-41 (3 pp.).

\* cited by examiner

METHOD AND DEVICE FOR WHITENING TEETH USING SONOCHEMISTRY

CROSS-REFERENCE TO RELATED APPLICATIONS

This application claims the benefit of application No. 61/428,804, filed Dec. 30, 2010, and which is incorporated herein by reference.

This application is a continuation-in-part of application Ser. No. 12/585,215, filed Sep. 8, 2009, which application Ser. No. 12/585,215 is a continuation-in-part of application Ser. No. 11/412,076, filed Apr. 27, 2006, now abandoned which application Ser. No. 11/412,076 claims the benefit of application No. 60/675,089, filed Apr. 27, 2005, and each of which is incorporated herein by reference.

FIELD OF THE INVENTION

The invention relates to a method and device for whitening teeth. More particularly, the invention relates to a method and device for whitening teeth by using ultrasonic energy applied to a whitening composition provided on a user's teeth. Still further, the invention even more particularly relates to a tooth whitening method, device, and system including an ultrasonic wave transducer for using sonochemistry to enhance the efficacy of a whitening composition provided on a user's teeth.

BACKGROUND OF THE INVENTION

There are known systems for whitening teeth using toothpaste with abrasives for removing extrinsic stains.

There are likewise known systems for whitening teeth using hydrogen peroxide.

There is a known attempt to whiten teeth using ultrasound by means of mechanical removal of extrinsic stains.

As further background, the following discussion regarding tooth structure and known whitening methods is provided.

Tooth enamel is predominately formed from an inorganic substance, hydroxyapatite crystals, along with approximately 5% organic materials, predominantly collagen. The dentin is composed of about 20% protein including collagen; the balance of inorganic materials including hydroxyapatite crystals. The acquired pellicle is a proteinaceous layer on the surface of tooth enamel, and that may be removed after an intensive tooth cleaning.

Tooth stains are generally classified as either extrinsic or intrinsic, depending on whether the stain is on the surface of the tooth within the acquired pellicle or within the tooth structure itself within the enamel or dentin. For example, extrinsic staining of the acquired pellicle can occur from foods or compounds, which contain tannins and other polyphenolic compounds which become trapped in the lightly bound proteinaceous layer on the surfaces of the teeth. Extrinsic tooth staining is removed by mechanical methods, such as by using abrasives applied by a toothbrush by a user on his or her teeth, or by a dental professional blasting a patient's teeth with an abrasive. A problem with these methods is that the consumer experiences minimal initial and longterm tooth whitening (e.g., 6 months).

Intrinsic staining, on the other hand, occurs when chromogens and pre-chromogens penetrate the enamel and dentin and become tightly bound to the tooth structure. Intrinsic staining can occur when blood or amalgam products leach into the enamel and dentin. Intrinsic staining likewise can occur systemically from excess fluoride intake during enamel development leading to a mottled yellow or brown stain of fluoresce staining. Intrinsic staining is not removable by mechanical methods of tooth cleaning and generally requires the use of chemicals, for example strong oxidizing agents such as hydrogen peroxide which can penetrate into the tooth structure to effect a change in the light absorbtivity of the stain chromogen and/or the solubility of the chromogens.

The desire for whiter, lighter teeth is considered to be cosmetic and desirable in today's cosmetically-orientated society. Tooth bleaching is generally accomplished by gels, pastes, or liquids which contain an oxidizing agent such as hydrogen peroxide ($H_2O_2$) that attack (i.e., chemically react with) the chromogen molecules, making them colorless and/or water soluble, making the tooth appear lighter and brighter, thus resulting in lighter brighter teeth.

The most commonly used oxidizing agent is hydrogen peroxide (H2O2), such as from carbamide peroxide ($CH_6N_2O_3$), which is mixed with an anhydrous viscous carrier containing glycerin, known as glycerol ($C_3H_8O_3$) and/or propylene glycol and/or polyethylene glycol ($C_3H_8O_2$). Sodium chlorite, chlorine dioxide, peracetic acid or ethaneperoxoic acid ($C_2H_4O_3$) may likewise be used as an oxidizing agent.

When in contact with water, carbamide peroxide dissociates into urea, also known as carbamide ($CH_4N_2O$) and hydrogen peroxide ($H_2O_2$). The hydrogen peroxide in the presence of water then dissociates into water and oxygen anions. It is these oxygen anions which react with the stain making them more water soluble, transparent, or both.

There are several known delivery systems to deliver carbamide peroxide, for example, to the surfaces of the teeth.

A common approach is to have a dental professional construct a custom-made tray from an impression of the patient's teeth. An oxidizing gel is dispensed into the tray by the patient and the tray is worn over the teeth intermittently for a period of days to several weeks, depending on the severity of the staining. This approach has been known to cause tooth sensitivity in over 60% of the users, and it can be uncomfortable for the users to wear the tooth bleaching trays. Tooth sensitivity is believed to result from the movement of fluid through the dentinal tubules, which is sensed by nerve endings within the tooth. The carriers, glycerin propylene glycol and polyethylene glycol, draw fluids toward them and therefore contribute to the tooth sensitivity often experienced by wearing a bleaching tray.

Another known approach is to incorporate an oxidizing agent in a strip and have the patient wear the strip intermittently over a period of two weeks. This approach also has had the disadvantage of being awkward for users to wear, and many users also experience tooth sensitivity. Further, the known strips have an inherent problem of contacting the teeth only on the facial surfaces and fail to remove the staining which occurs in between the teeth in the interproximal areas.

Other known methods of intrinsic whitening include applying the whitening compound directly on the user's teeth which is easy for the user to apply but still takes several days to achieve desired results.

It can thus be seen that there is a need for a more effective and even faster tooth whitening device and method that provide enhanced tooth whitening results.

There are known tooth whitening devices, methods, and compositions that use heat and light to accelerate the tooth whitening chemical reactions. Another known method of intrinsic whitening is using non-heat light energy to activate a photo initiator in the whitening solution therefore accelerating the whitening result.

As used herein, sonochemistry relates to the effect of ultrasonic waves on chemical reactions. Chemical effects of ultrasound arise from changes, such as acoustically induced cavitation and induced temperature rises in a composition, rather than from a direct interaction with a molecule in question. It is that enhancement of a chemical reaction which is used to synergistically enhance the chemical effect on the whitening of teeth in the present invention. See, e.g., Practical Sonochemistry Power Ultrasound Uses and Applications Mason, Timothy J. et al., Hoorwood, 2nd Ed., 2003, ISBN: 978-1-898563-83-9.

OBJECTS AND SUMMARY OF THE INVENTION

An object of the invention is to overcome the drawbacks of the prior art.

Another object of the invention is to use sonochemistry in the whitening of teeth.

A further object of the invention is to provide an ultrasonic tooth whitening device which generates a sufficiently high ultrasonic frequency so as to achieve the desired enhancement of the chemical reaction required for whitening the enamel or dentin of the user's tooth, or both, by achieving a desired cavitation of a tooth whitening composition having a tooth whitening compound therein and held by a liquid retaining element, such as a sponge, adjacent of the user's teeth; namely, so as to optimize and enhance the chemical reaction of the tooth whitening compound in the tooth whitening composition in contact with the user's teeth.

It is another object of the invention to use an ultrasonic tooth whitening device which generates ultrasonic frequencies to enhance the chemical activity of the whitening compound to increase the efficacy of the tooth whitening compound, and to reduce treatment time, and, hence, enhance the tooth whitening effect of the tooth whitening composition, and to do such in ultrasonic frequencies in the range of about 20-100 kHz.

A further object of the invention is to provide an ultrasonic tooth whitening device which generates a sufficiently high ultrasonic frequency or an ultrasonic frequency selected so as to enhance the chemical reaction required for whitening the enamel or dentin of the user's tooth, or both, by achieving a desired cavitation of the tooth whitening composition held by the liquid retaining element adjacent of the user's teeth; namely, so as to optimize and enhance the chemical reaction of the tooth whitening compound in contact with the user's teeth. Cavitation is the formation of bubbles in a liquid. Cavitation may be induced by an energy input, such as acoustical energy; e.g., by ultrasonic energy. As used herein, the invention includes the enhanced tooth whitening using chemical tooth whitening thanks to the synergistically enhanced chemical reactions resulting from the use of sonochemistry inducing the cavitation to speed up and enhance the chemical whitening of a user's teeth. That is, to enhance the whitening of both intrinsic and extrinsic stains on a user's teeth.

It is yet another object of the invention to provide a device which includes the liquid retaining device or element configured as a sponge conforming to irregularities of tooth dentition and configured to ensure that a whitening compound in a whitening composition retained by the liquid retaining element is provided adjacent to interstices between a user's teeth for whitening visible portions between the user's teeth.

It is yet another object of the invention to provide a device which includes liquid retaining element configured as an open-cell sponge to enhance the retention of a whitening composition retained by the sponge and enhance the accelerated chemical reactions which whiten the user's teeth when the device is applied to a user's teeth.

It is another object of the invention to use an ultrasonic tooth whitening device which enhances the tooth whitening effect of the tooth whitening composition, and operates in the range of about 20-100 kHz.

Another object of the invention is to provide a more rapid and environmentally friendly, as well as less irritating method and device for tooth whitening.

It is another object of the invention to have the ultrasonic method and device work with additional compositions to treat other oral issues; i.e., periodontal disease, gingivitis, peritonitis, halitosis, and the like.

These and other objects of the invention will be apparent from a consideration of applicant's description and drawings.

In sum, the invention includes a tooth whitening device and tooth whitening composition containing a tooth whitening compound. The device for whitening teeth includes an ultrasonic generator or transducer, the ultrasonic transducer including an ultrasonic horn, the ultrasonic transducer and horn being sized and configured for generating and transmitting at least about twenty kHz. The ultrasonic horn is configured for transmitting ultrasound into a liquid tooth whitening composition, or for providing a liquid tooth whitening composition adjacent a user's teeth, or for both transmitting ultrasound into a liquid tooth whitening composition and providing a liquid tooth whitening composition adjacent a user's teeth, in use.

The inventive method and device for whitening teeth using sonochemistry includes the enhancing of the effects of the chemical whitening of teeth as opposed to known methods of cleaning teeth using purely mechanical cleaning of the teeth. (For example, there is a known method of scraping away plaque and tartar using a small mechanical scraping tool which is vibrated thousands of times per second by a so-called ultrasonic transducer. That is, the mechanical stroke or reciprocation of that known driven tooth scraping tool is used to remove extrinsic material, such as tartar and plaque. Thus, that known mechanically driven tool inherently removes some extrinsic discoloration or extrinsic stains on a patient's teeth by mechanical means.) In the present invention, however, the chemical whitening of both intrinsic and extrinsic stains is enhanced by driving the chemical reaction at a greater rate than was previously known. This speeding up of the chemical reaction thanks to the rapid development of and following implosions of cavitation bubbles produce rapid heat in a microscopic localized area adjacent the patient's teeth in accordance with the invention.

That is, applicant's liquid retaining element is for retaining the whitening composition adjacent to and providing the inventive whitening composition on the patient's teeth, and the invention applies sonochemistry to enhance the whitening effect, as will be appreciated from the specification as a whole, and can be seen graphically in FIG. 9 set forth and described below. This use of sonochemistry to enhance the chemical whitening of a patient's teeth has been heretofore unknown.

The tooth whitening device according to the invention may likewise include an ultrasonic horn configured for being held adjacent to the user's teeth and for retaining a liquid tooth whitening composition adjacent the teeth.

The tooth whitening horn may be configured as an arch shaped ultrasonic horn for ensuring that the tooth whitening composition held thereby is provided adjacent to one or more of the user's teeth. The tooth whitening device may include a horn configured for retaining a detachable or fixed liquid retaining element, such as a sponge or fabric pad for retaining a tooth whitening composition.

The device may further include a sponge which is an open cell sponge for retaining the tooth whitening composition adjacent the user's teeth. The open-cell sponge may be supplied to the user already pre-moistened with a whitening composition, or the sponge and whitening composition may be provided separately to the user for the user to apply the whitening composition to the sponge or foam pad.

The sponge may also be reusable, either for a series of treatment cycles, or for different applications of the treatment cycles.

The ultrasonic whitening device would be used in such a way that the user would attach a liquid retaining element configured as a pre-moistened, disposable foam strip to the ultrasonic horn. The user would then hold the device in such a way so that the foam strip is pressed against their teeth. The device would activate the ultrasonic energy for a predetermined number of minutes, for example, between 1 and 20 minutes. After the device stops, the user would then change the foam strip to a new pre-moistened foam or add fresh amount of whitening composition to the foam strip. The user would then repeat the process of holding the device up to his or her mouth so that the foam pad is pressed against the teeth for another treatment cycle. The process would be repeated for between 1 and 20 treatment cycles, as required.

In sum, the invention one of comprises, includes, consists essentially of, and consists of a tooth whitening device for whitening teeth using sonochemistry having a body, and an ultrasonic transducer provided in the body, the ultrasonic transducer being configured for producing ultrasonic waves of a sufficient frequency to induce a sonochemical reaction in a liquid tooth whitening composition. The device further includes an ultrasonic horn provided on the body and operatively connected with the ultrasonic transducer for transmitting ultrasonic waves into a liquid tooth whitening composition, and a liquid retaining element provided on the ultrasonic horn. The liquid retaining element is configured for retaining a liquid tooth whitening composition against a user's teeth during a sonochemical reaction induced by ultrasonic waves.

The inventive tooth whitening device likewise includes that the liquid retaining element is a sponge, such as an open-cell sponge.

The inventive tooth whitening device likewise includes that the liquid retaining element includes an absorbent material, which may be detachably attached to the ultrasonic horn.

The inventive tooth whitening device likewise includes that the ultrasonic horn is substantially curved and configured for following a contour of a user's outer front teeth.

The inventive tooth whitening device likewise includes that the ultrasonic horn includes a free end, and the liquid retaining element includes a liquid retaining foam pad detachably attached to the ultrasonic horn by use of a detachable element provided on the detachable foam pad.

The inventive tooth whitening device likewise includes that the detachable element includes a sleeve configured for being attached to a free end of the ultrasonic horn.

The inventive tooth whitening device likewise includes that the liquid retaining element includes a detachably attached liquid retaining material including a liquid tooth whitening composition provided therein.

The inventive method for whitening teeth using sonochemistry includes the steps of providing a tooth whitening device, the tooth whitening device having a body and an ultrasonic transducer provided in the body. The ultrasonic transducer is configured for producing ultrasonic waves of a sufficient frequency to induce a sonochemical reaction in a liquid tooth whitening composition. There is an ultrasonic horn provided on the body, the ultrasonic horn being operatively connected with the ultrasonic transducer for transmitting ultrasonic waves into a liquid tooth whitening composition. There is likewise a liquid retaining element provided on the ultrasonic horn, the liquid retaining element being configured for retaining a liquid tooth whitening composition against a user's teeth during a sonochemical reaction induced by ultrasonic waves. The method further includes providing a liquid tooth whitening composition on the liquid retaining element, causing the ultrasonic horn to be vibrated at a sufficient ultrasonic frequency to induce a sonochemical reaction in a liquid tooth whitening compositions, and placing liquid tooth whitening composition on the liquid retaining element and holding the liquid tooth whitening composition on the liquid retaining element adjacent the user's teeth for a predetermined period of time.

The inventive method for whitening teeth using sonochemistry further includes that to induce a sonochemical reaction in a liquid tooth whitening composition, the ultrasonic horn is vibrated at an ultrasonic frequency of 20-100 kHz, such as at an ultrasonic frequency of about 40 kHz.

The inventive method for whitening teeth using sonochemistry further includes that the liquid tooth whitening composition includes an oxidizing agent, and the oxidizing agent is one of hydrogen peroxide, carbamide peroxide, sodium chlorite, chlorine dioxide and peracetic acid.

The inventive method for whitening teeth using sonochemistry further includes that the liquid tooth whitening composition held adjacent the user's teeth includes a hydrogen peroxide, or a carbamide peroxide, percentage in a range of about 0.01-35.0%.

The inventive method for whitening teeth using sonochemistry further includes that the liquid tooth whitening composition held adjacent the user's teeth includes a hydrogen peroxide percentage of at least about 3.0%, or at least about 6.0%, depending on the intended use.

The inventive method for whitening teeth using sonochemistry further includes that the liquid tooth whitening composition held adjacent the user's teeth includes a water percentage of about 82.8%, and hydrogen peroxide 35% sol percentage of 17.15%, a sodium hydroxide percentage of about 0.05%.

The inventive method for whitening teeth using sonochemistry further includes that a power supply for the ultrasonic transducer is provided in the body, an indicator light is provided in the body, and control circuitry is operatively connected to the power supply and to the indicator light for controlling operation thereof.

The inventive method for whitening teeth using sonochemistry further includes that the body is configured for being handheld during operation thereof.

The inventive method for whitening teeth using sonochemistry further includes that the liquid retaining element is detachably attached to the ultrasonic horn. The liquid retaining element may be supplied to the user already moistened with the liquid tooth whitening composition.

The inventive method for whitening teeth using sonochemistry further includes that the ultrasonic horn, and the liquid retaining element are configured to ensure that the liquid tooth whitening composition avoids contact with the gums and other mouth tissues to ensure the liquid tooth whitening composition avoids harming the gums and mouth tissues, and also avoids the killing of mouth flora.

These and other objects of the invention will be apparent from a consideration of applicant's written description and drawings.

In this invention the ultrasound is used to enhance the chemical reaction that takes place during tooth whitening. This enhancement of a chemical reaction subjected to ultrasonic energy is known in the field of sonochemistry. There are different mechanisms that allow sonochemistry to enhance the whitening treatment.

First, one result of taking advantage of applying ultrasonic energy to the composition is the generation of and implosion of cavitation bubbles and resultant intense heat in a localized area. It is well known that adding heat to a chemical reaction will accelerate the reaction. An advantage of the system set forth herein is the heat produced is at a high temperature, but has a small heat capacity. The heat will accelerate the reaction, but not change the overall temperature of the solution very much. Some other methods of tooth whitening will heat up the whitening solution until it is uncomfortable for the user.

Second, when such a cavitation bubble forms and then implodes on a hard surface, the liquid surrounding the bubble is forced against the surface at a high rate of speed. This has two effects, first it will remove any surface imperfections and expose a clean surface for the chemical reaction; and second, it can drive the chemistry, so to speak, (e.g., the chemical reaction) further into the solid surface.

The ultrasonic tooth whitening device and method according to the invention may include a handheld rechargeable battery powered device, or the device may be directly plugged into a conventional wall outlet, and may contain an ultrasonic transducer, be held and manipulated by a user, and have a custom ultrasonic horn for transmitting ultrasonic energy on its working end.

Another option for the device would be for there to be a control unit that would be able to sit on a desk or counter. This unit may be plugged into a wall outlet or contain rechargeable batteries. The control unit may also contain the control circuits for the device. This unit may be connected by a wire to a handheld device that would contain the ultrasonic transducer and horn.

The hand held portion may also contain a light visible to the user to indicate when the unit is in an operational mode. The light may be on top of the device and furthest from the mouth, in use, in order for the user to see the light. The light could also give other information to the user by flashing, changing the rate of flashing, or changing the intensity of the light, to indicate how long the treatment cycle has been, how much more time there is until the treatment is done, and other information. For example, one such scenario would be that the light is programmed to blink once every 30 seconds and then blink continuously for the last 30 seconds of the treatment cycle. Another scenario would be for the light to slowly get brighter during the treatment, and then flash for the last minute of use.

It is further contemplated that the light may change color in addition to or instead of changing brightness, or turning on and off.

The device may also include an audible indicator to provide information to the user. For example, the device may "beep" when first turned on and then every 30 seconds after that. There may be a cycle with 2 beeps after 30 seconds, 3 beeps after a minute, 4 beeps after 90 seconds, and so on. Another scenario would be for the audible indicator to get louder or the beeps more frequent to indicate either the passage of time or the approaching of the end of a treatment cycle.

The audible indicator may also be used for providing "spoken" words to give the user instructions, or indications of progress. Examples of spoken words include "One minute has passed", "Two minutes remain", "You have completed 3 cycles", and the like.

This unit may be used either by a consumer in his or her home or by a dental professional in a dental office.

The control unit may also have one or more displays indicating to the user such things as for how much time the device has been operating, how much time is left in the current treatment cycle, how many treatment cycles have been completed, or how many treatment cycles remain.

The ultrasonic horn may be in the shape of an arch. The arch may conform to a face of a user's anterior teeth; e.g., front teeth. Covering the arch may be an open cell sponge which may be saturated with a tooth whitening solution. When the sponge is pressed against the teeth, the ultrasonic horn will generate cavitation bubbles within the whitening composition in the sponge. The configuration of the ultrasonic horn is also such that the ultrasonic energy is transmitted along the whole of the arch to spread the sonochemistry effect to all of the teeth touching the sponge. This design is made possible and verified through the use of one of the commercially available finite element analysis program that specializes in ultrasonic horn design.

The ultrasonic horn, and the liquid retaining element are configured to ensure that the tooth whitening composition avoids contact with the gums and other mouth tissues; such ensures that the whitening composition avoids possibly harming the gums and mouth tissues, and also avoids the killing of mouth flora; e.g., beneficial and harmful mouth flora, such as bacteria.

The ultrasonic horn may be made of metals, such as aluminum, stainless steel, and titanium. It is also possible for the horn to be made of hard plastics such as polycarbonate, PEEK (polyether ether ketone), and ULTEM™ (a PEI (polyetherimide) product from SABIC, www.sabic.com, ULTEM® is a trademark of SABIC Innovative Plastics Holding BV, The Netherlands).

In our testing, good results have been obtained when the system produces a movement in the horn of approximately 0.0006" (about 0.015 mm), measured peak to peak. This amount of motion allows for the formation of cavitation bubbles. Other amounts of motion that allow for cavitation could also be used.

The ultrasonic horn may be configured to engage and whiten either the top or the bottom teeth, or both.

The batteries may be one of a number of known rechargeable or nonrechargeable types.

The handle may be configured to receive and hold a toothbrush attachment so that the handle may also be used for daily tooth brushing in addition to being used for tooth whitening treatments.

The hand held device, either a device that is entirely contained in the handle, or a device that has a portion that is handheld and a separate base unit that is connected by a cord, may have substantially two parts. The first part may include the ultrasonic horn and the ultrasonic transducer. This portion may point substantially straight out from the mouth, in use, so that the ultrasonic energy from the transducer may be directed towards the teeth. The second portion of the handheld device may be the handle portion. This portion may include electronics or batteries. An angle between the ultrasonic transducer portion and the handle portion has been chosen to provide an ergonomic benefit to the user. Our research suggests that if the angle is an acute angle, it allows the user to rest his or her whole arm against the chest area. This facilitates holding the device during the required length treatment.

The handle may have a small pump and reservoir of the whitening composition. During treatments, the device may be used to add whitening composition to the sponge so that there will be more "fresh" solution available.

The same or different pump may be used to remove "spent" whitening composition from the sponge. This may go to an additional reservoir in the handle.

In that case, those two reservoirs may include a removable and replaceable cartridge. The two separate reservoirs may share a common moveable wall, or the reservoirs may be configured as collapsible bags, so that as whitening composition is pumped out of the supply reservoir, space would be available in the return reservoir.

Relative terms, such as left, right, up, and down are for convenience only and are not intended to be limiting.

DETAILED DESCRIPTION OF THE INVENTION

Embodiments of the invention are set forth in FIGS. 1-11.

Figures 1, 2:
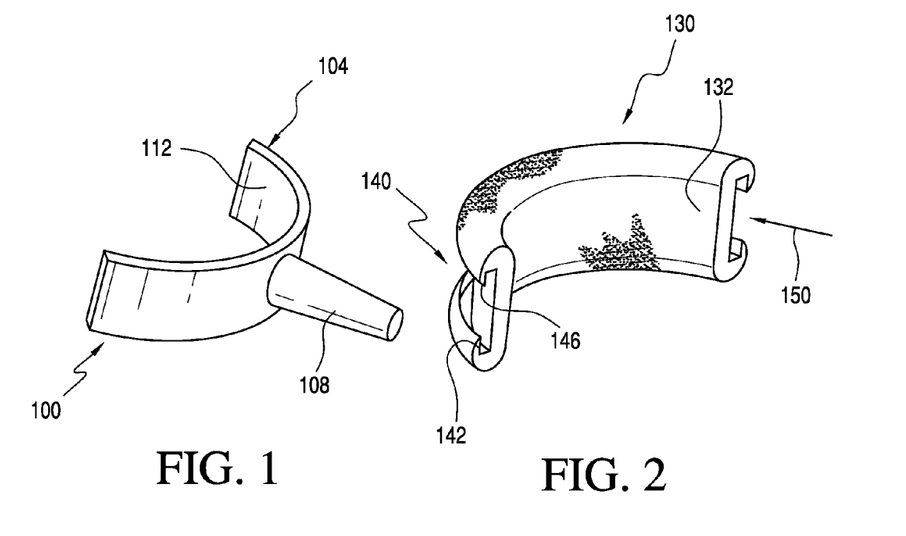
FIG. 1 is a front perspective view of an ultrasonic horn configured as an arch in accordance with an embodiment of the invention.
FIG. 2 is a rear perspective view of a sponge for retaining a tooth whitening composition and configured as an arch that may be retained by the arch-shaped ultrasonic horn according to the invention.
Figure 3:
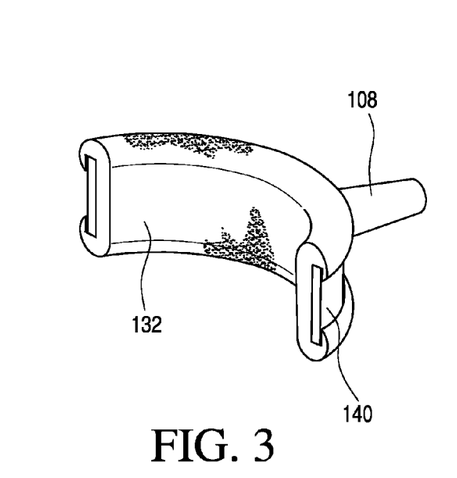
FIG. 3 is a rear perspective view of the sponge of FIG. 2 in place on the arch-shaped ultrasonic horn of FIG. 1 in accordance with the invention.

A device for whitening teeth may include an ultrasonic horn. The ultrasonic horn 100 is configured for transmitting ultrasound energy into a tooth whitening composition that is activated by ultrasonic energy, or for providing a tooth whitening composition adjacent a user's teeth, or for both transmitting ultrasound into a liquid tooth whitening composition and providing a liquid tooth whitening composition adjacent a user's teeth, in use.

The tooth whitening horn 100 may be configured to include an arch-shaped surface 104 for ensuring that the tooth whitening composition held thereby is provided adjacent to one or more of the user's teeth. An insert 108, such as the illustrated male insert 108, may be used to attach horn 100 to an ultrasonic transducer or generator, as shown below in FIGS. 5-8. Insert 108 may be detachable. A free end 112 of horn 100 may be used to assist in detachably attaching a liquid retaining element 130 to the arch-shaped horn 100. The arch-shaped surface 104 may conform to a face of a user's anterior teeth; e.g., front teeth. Covering the arch may be a liquid retaining device or element or open cell sponge 130 for retaining a tooth whitening composition, and which may be saturated with a liquid tooth whitening composition.

Sponge 130 may have an inner face 132 conforming to the user's teeth.

Sponge 130 may include a slot 140 having a lower extension 142 and an upper extension 146. Slot 140 may be configured for receiving arch-shaped portion 104 of horn 100 so that sponge 130 is detachably retained by horn 100, such as by inserting free end 112 of horn 100 in the direction of an arrow 150 as shown in FIG. 2, as will be readily appreciated.

Figure 4:
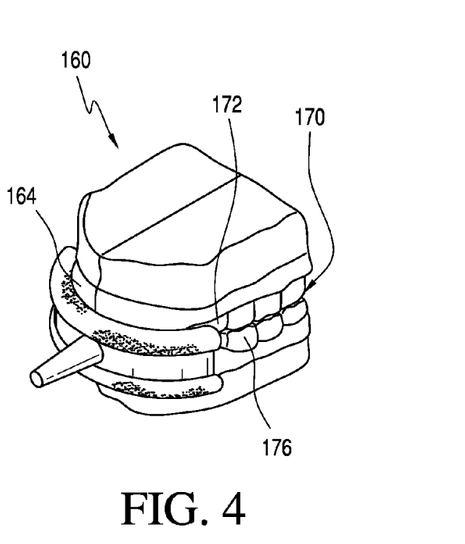
FIG. 4 is a front perspective view of the arch-shaped sponge in place on the ultrasonic horn of FIG. 3 and adjacent a user's teeth in accordance with the invention.

FIG. 4 shows arch-shaped horn 100 with sponge 130 attached thereto and tooth whitening composition retained by sponge 130 as it is held in place in use, as shown by a portion of user's mouth 160.

User's mouth 160 will include gums 164 and teeth 170. Teeth 170 may typically include front teeth, such as illustrated upper front teeth 172 and lower front teeth 176. The frontmost anterior teeth of teeth 170 are hidden from view in FIG. 4 as they are behind sponge 130, in use, as will be readily appreciated. Liquid retaining element 130 in accordance with the invention may be sized to cover the front 6, 8, 10 or 12 teeth, for example, for someone with typical dentition. Sponge 130 may cover both the top and bottom teeth 172 and 176 at the same time, as shown, or may only cover one arch of teeth at a time. Sponge 130 is configured so as to avoid contact with the user's gums 164, in use, so that the tooth whitening composition held by the inventive sponge 130 will likewise avoid contact with gums 164, to ensure that the tooth whitening composition avoids possibly harming gums 164 and mouth tissues, and also avoids the killing of mouth flora; e.g., beneficial and harmful mouth flora, such as bacteria, as will be appreciated.

Figures 5, 6:
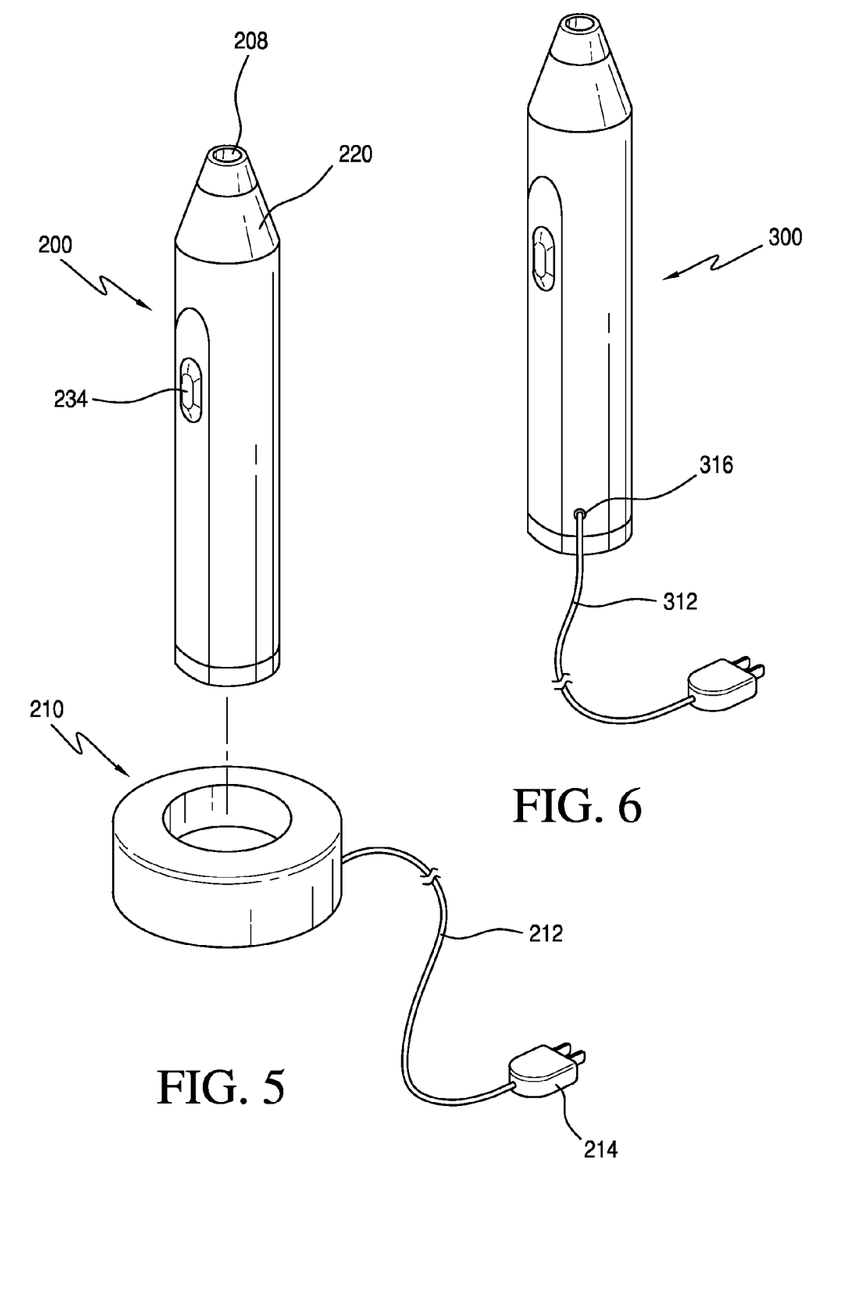
FIG. 5 is a partially exploded perspective view of a handheld rechargeable battery powered ultrasonic transducer for retaining and vibrating the ultrasonic horn in accordance with the invention, as well as a recharging base according to the invention.
FIG. 6 illustrates another embodiment of a handheld ultrasonic transducer in accordance with the invention that may be plugged in directly to a power source.

FIG. 5 illustrates an embodiment of a portable ultrasonic transducer 200 in the form of a rechargeable ultrasonic transducer including containing an ultrasonic transducer (not visible in Figs.) and for being held and manipulated by a user that may have all or part of an ultrasonic transducer 220 for transmitting ultrasonic energy on its working end. The ultrasonic frequency may range from 20 to 100 kHz, and indeed from 22 kHz to 80 kHz, and may be controlled to operate between 20 and 60 kHz, and about 40 kHz, and about 25 to 45 kHz, or that sweeps between any of those frequency ranges, depending on the intended use.

The hand held device 200 may include an ON/OFF switch 234 for controlling operation of the device 200, and device 200 may also be configured to receive and hold a toothbrush attachment likewise by use of a female insert or receptacle 208 configured for receiving male insert 108 of horn 100 of FIG. 1, so that the handle may also be used for daily tooth brushing in addition to being used for tooth whitening treatments.

The ultrasonic tooth whitening device 200 may be a handheld rechargeable battery-powered device.

The FIG. 5 embodiment may likewise include a charging base 210 supplied with electricity by an electrical cord 212 and a conventional plug 214 for insertion into a household receptacle.

FIG. 6 illustrates another embodiment of hand-held ultrasonic generator 300 which may be likewise charged by use of an electric cord 312 and a detachable connector 316, as will be readily understood.

Figure 7:
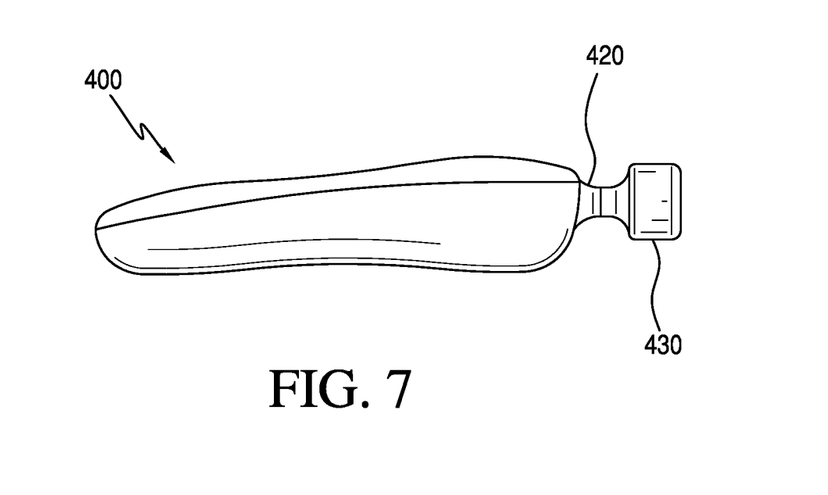
FIG. 7 is a perspective view of another embodiment of a handheld rechargeable battery powered ultrasonic transducer for retaining and vibrating the ultrasonic horn in accordance with the invention.

FIG. 7 illustrates another embodiment of a hand-held ultrasonic transducer 400 including an ultrasonic transducer having an external portion 420 and an ultrasonic horn 430. It will be appreciated that ultrasonic horn 430 viewed on its side is as shown. When viewed from above, it may be substantially arch-shaped, such as arch-shaped ultrasonic horn 104 of FIG. 1.

Figure 8:
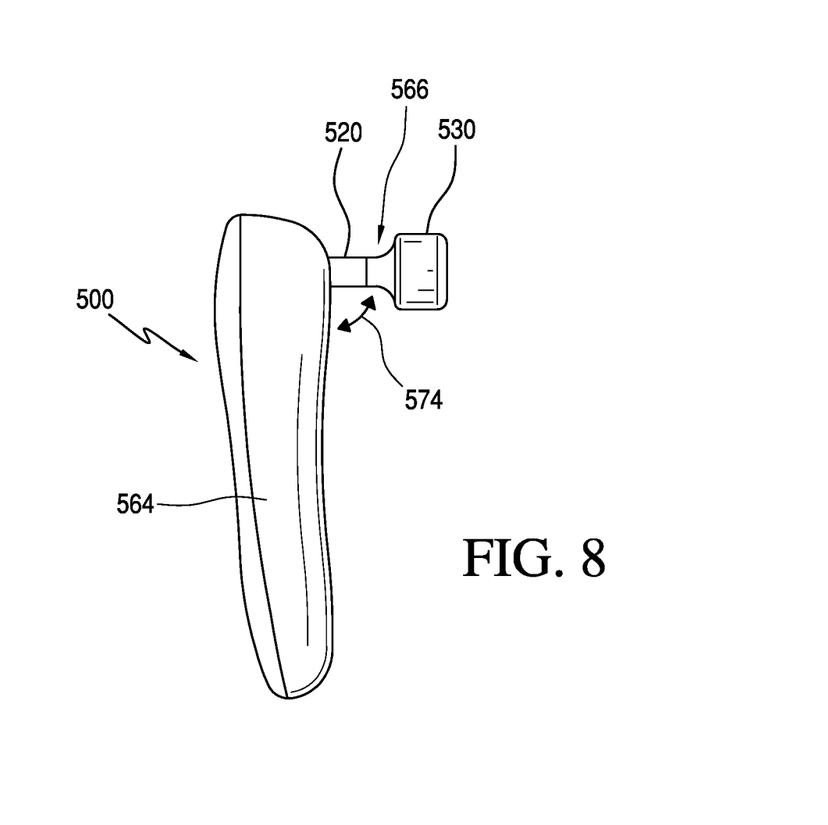
FIG. 8 is a perspective view of another embodiment of a handheld rechargeable battery powered ultrasonic transducer for retaining and vibrating the ultrasonic horn in accordance with the invention.

FIG. 8 illustrates another embodiment of a hand-held ultrasonic transducer 500 including an ultrasonic transducer 520 extending transversally relative to the handheld body portion of device 500, and an ultrasonic horn 530 on the end of transducer 520 that is analogous to that described in connection with the embodiment of FIG. 7.

The device 500 may include a grip portion 564 and an outwardly extending portion 566 that will interface with the mouth. As show, an angle 574, such as a right angle or an acute angle, may be defined between grip portion 564 and outwardly extending portion 566. Angle 574 may be between 60 and 89 degrees, between 70 and 80 degrees, and indeed about 75 degrees. Those angles will all enhance the usability of whitening device 500.

Figure 9:
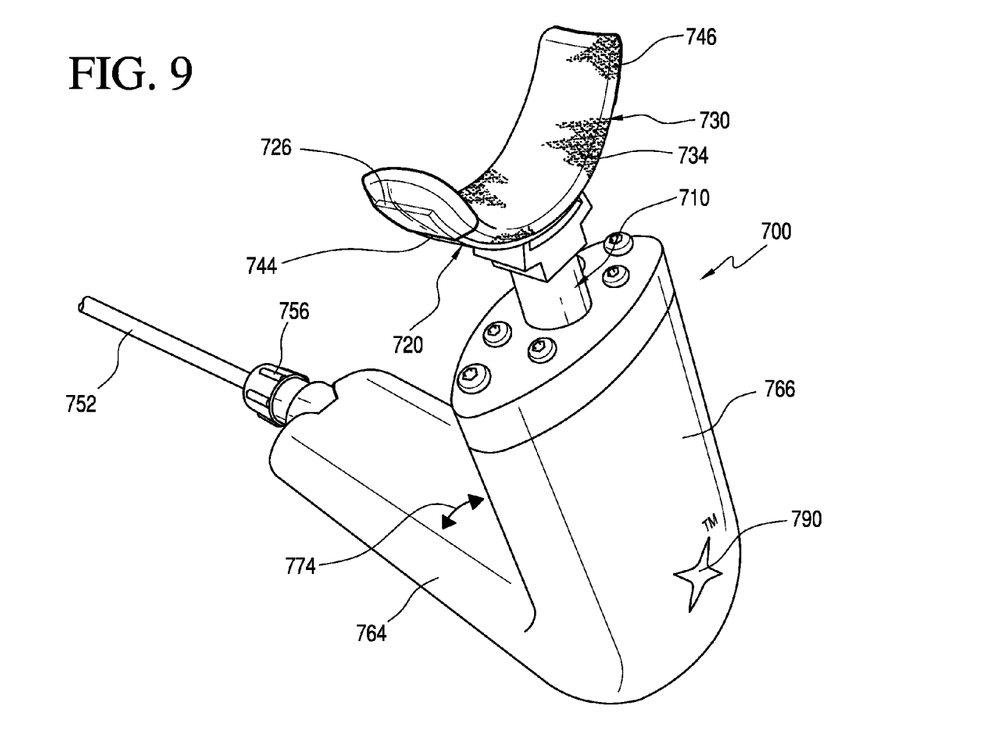
FIG. 9 is a further embodiment of a handheld powered ultrasonic tooth whitening device.

FIG. 9 illustrates another embodiment of an ultrasonic tooth whitening device 700 using sonochemistry to enhance the effectiveness of a tooth whitening composition and method according to the invention. Device 700 may include an ultrasonic transducer 710 and an ultrasonic horn 720 operatively associated therewith. Ultrasonic horn 720 may include a free end or first free end 726, and a spaced apart second free end, as shown. A liquid retaining element such as the illustrated sponge 730 may be provided on ultrasonic horn 720, in use. Sponge 730 may include a liquid retaining material 734, such as an open cell foam. To enhance the usability, and to make sponge 730 readily replaceable by the user, a detachable fastener, such as a hook-and-loop faster, or the illustrated first sleeve 744, may be provided and configured for engaging with first free end 726 of ultrasonic horn 720. In that manner, the user may readily add and replace liquid retaining element 730, as needed. Sleeve 744 may be clear, as shown, or may be opaque. A further or second sleeve 746 may be provided for engaging with the second free end of ultrasonic horn 720, depending on the intended use Ultrasonic transducer 710 may be powered by a battery, not shown, or by electricity available from an outlet, via a power cord 752 which may be detachably attached to the remainder of ultrasonic whitening device 700 thanks to a coupling element 756, as shown. Depending on the intended use, standard household current of 115V AC or 230V AC may be used, or direct current such as provided by a known AC/DC converter, as will be readily appreciated.

The device 700 may include a grip portion 764 and an outwardly extending portion 766 that will interface with the mouth. As show, an angle 774, such as a right angle or an acute angle, may be defined between grip portion 764 and outwardly extending portion 766 holding the ultrasonic horn 720 which holds liquid retaining element 730 in its desired position adjacent the user's mouth. Angle 774 may be between 60 and 89 degrees, between 70 and 80 degrees, and indeed about 75 degrees for enhancing the usability of whitening device 700.

The hand held portion may also contain a light 790 visible to the user to indicate when the unit is in an operational mode. Light 790 may be on top of the device and furthest from the mouth, in use, in order for the user to see light 790. The light could also give other information to the user by flashing, changing the rate of flashing, or changing the intensity of the light, to indicate how long the treatment cycle has been, how much more time there is until the treatment is done, and other information. For example, one such scenario would be that the light 790 is programmed to blink once every 30 seconds and then blink continuously for the last 30 seconds of the treatment cycle. Another scenario would be for the light to slowly get brighter during the treatment, and then flash for the last minute of use.

It is further contemplated that light 790 may change color in addition to or instead of changing brightness, or turning on and off. It is further contemplated that a speaker may be used in addition to or instead to of light 790 to "speak" the amount of time remaining to the user, and/or the number of treatments remaining, and the like. Light 790 is shown in the form of a star which is a trademark of Dentovations Inc., Boston, Mass., United States (US) (www.dentovations.com).

Figure 10:
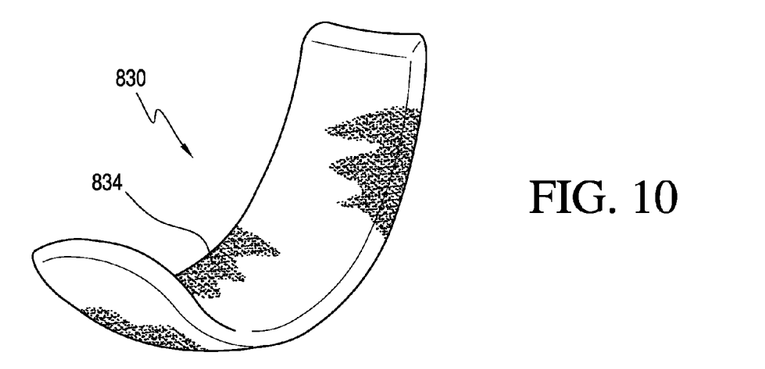
FIG. 10 is a perspective view of another embodiment of a liquid retaining element.

FIG. 10 illustrates a further embodiment of a liquid retaining element 830 in the form of a replaceable liquid retaining pad 834. Pad 834 may be made of a liquid retaining fabric, as shown, or a foam as in the embodiment of FIG. 9. Further, the pad 830 may be preloaded with a liquid whitening composition for ease of use by a consumer, and the pad 830 may be detachably attached to ultrasonic horn 730 such as by an adhesive or detachable double-sided tape, not visible in the prospective view of FIG. 10.

It is also possible for the handheld ultrasonic transducer to have a small pump and reservoir of the whitening composition. During treatments, the device may add whitening composition to the sponge so that there will be more "fresh" unreacted solution available.

It is also possible to use the same or different pump to remove "spent" reacted whitening composition from the sponge. This may go to an additional reservoir in the handle.

Those two reservoirs may include a removable and replaceable cartridge. The two separate reservoirs may either share a common moveable wall, or the reservoirs may be configured as collapsible bags, such that as whitening composition is pumped out of the supply reservoir, space would be available in the return reservoir.

The handle may contain batteries, control electronics, and the ultrasonic transducer. The transducer may be either a magnetostrictive or a piezoelectric type. A transducer which may be used is the Hainertec HNC-8SS-2540 supplied by Hainertec (Suzhou) Co., Ltd., Jiangsu, China.

It is known with ultrasonic systems that often times they run at a fixed frequency near the resonance frequency of the transducer. Other systems will vary the frequency between 2 different frequencies. It may switch back and forth between the frequencies or have more than one frequency operating at a time. Still other systems will vary the frequency of the system so that is continuously moving between two frequencies.

Other ultrasonic systems, especially ones that are battery powered, employ a system where the transducer will turn on and off during use. The duration of the ON and OFF cycles could be in the micro-second to millisecond range. This has the advantage of saving power, while the enhancing of the chemical reaction will continue during the periods that the transducer is off.

Good results have been achieved with a whitening composition in accordance with the invention.

Figure 11:
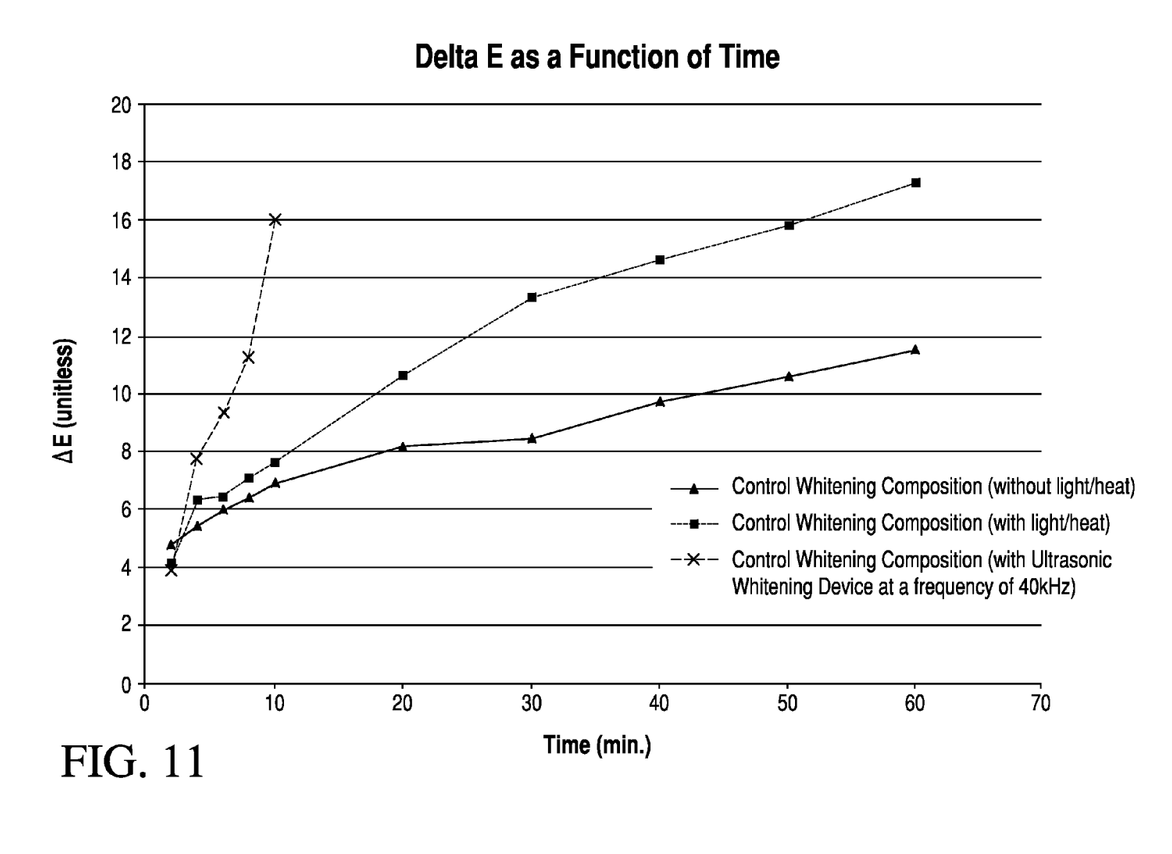
FIG. 11 is a graph schematically representing the test results of the whitening of a control tooth in a whitening composition and whitened in accordance with the ultrasonic tooth whitening method according to the invention, as compared to a control tooth in the whitening composition and whitened by the application of heat and light, and as compared to a control tooth in the whitening composition and whitened without the application of heat and light. The control tooth whitening composition used for whitening each of the three teeth of that FIG. 11 test was "Whitening Agent Composition A5" as set forth in col. 8, lines 20-30 of the Dentovations Inc. U.S. Pat. No. 6,517,350 to Diasti et al., and which is incorporated herein by reference. In brief, the whitening composition used in FIG. 11 included urea hydrogen peroxide of about 11% by weight, which yielded hydrogen peroxide of about 3% by weight.

Set forth in FIG. 11 is a graph showing the resultant change in color between two control artificially stained bovine teeth treated with and without heat and light, respectively, by one of applicant's tooth whitening compositions (i.e., "Whitening Agent A5") of U.S. Pat. No. 6,517,350 as set forth above, and a third artificially stained bovine tooth treated by the same whitening composition and with the application of ultrasonic waves (at 40 kHz) according to the invention. The two bovine control test teeth were treated for equal periods of time (60 minutes). The third bovine test tooth was treated using sonochemistry induced by the ultrasonic tooth whitening device according to the invention. The bovine test tooth was treated with the ultrasonic tooth whitening device for ten (10) minutes, as after ten (10) minutes the whitening of that third tooth using ultrasonic was the same as after about 50-60 minutes, respectively, with the two control teeth. The control teeth and the ultrasonically treated test tooth both had a similar color at the outset (Delta E=0; time=0). The test tooth was then subjected to the ultrasonic energy; i.e., ultrasonic energy generated by a 40 kHz ultrasonic transducer in accordance with the invention. The color of the tooth was measured before and after treatment at various intervals, as shown, perceivable by a human. Delta E is a standard way of calculating color difference perceivable by a human.

The International Commission on Illumination (CIE) terms its difference metric $\Delta E^*ab$ (also called $\Delta E^*$ or $dE^*$ or "Delta E") where delta denotes difference, and E stands for Empfindung; i.e., German for "sensation"; as in sensing or perceiving. The CIE76 definition established by the CIE was used. Delta E is unitless. A Konica-Minolta CM-700 spectrophotometer was used to measure the tooth color.

Laboratory tests using standard ultrasonic baths and probes that range in frequency from 22 kHz to 80 kHz have been conducted. It has been demonstrated that the addition of ultrasonic energy to the chemical reaction accelerates the desired chemical reaction at the full range of frequencies. As will be readily appreciated, 20 kHz is considered to be the low end of the frequency range that will form cavitation bubbles. Above 100 kHz, the cavitation bubbles still form, but they are of relatively small size.

In the following examples, the International Nomenclature of Cosmetic Ingredients (INCI) nomenclature has been set forth for ease of understanding.

In the following examples, the International Nomenclature of Cosmetic Ingredients (INCI) nomenclature has been set forth for ease of understanding.

The whitening composition in accordance with the invention may include hydrogen peroxide as the whitening compound. Good results have been achieved with the whitening composition of Example 1 detailed below, in which the hydrogen peroxide percentage in the composition is 6%.

Whitening Composition of Example 1

| Trade Name | INCI Name | Weight (%) |
| --- | --- | --- |
| Water | Water | 82.80 |
| Hydrogen Peroxide 35% sol | Hydrogen Peroxide | 17.15 |
| Sodium hydroxide (30% sol) | Sodium Hydroxide | 0.05 |
| Total | | 100.00 |

The hydrogen peroxide percentage in the composition of Example 1 is 6%, and additional examples of compositions according to the invention may have a hydrogen peroxide percentage which ranges from about 0.05-10.0%.

Good results have been achieved with a hydrogen peroxide based whitening composition, such as set forth in the composition of Example 1 in accordance with the invention.

The ultrasonic whitening device in accordance with the invention has been shown to achieve an increase in tooth whitening as measured by Delta E with all hydrogen peroxide-based whitening compositions and, indeed, all oxidizing agent-based whitening compositions tested.

Whitening Composition of Example 2

| Trade Name | INCI Name | Weight (%) |
| --- | --- | --- |
| Ethanol | Alcohol | 60.00 |
| Propylene Glycol | Propylene Glycol | 25.00 |
| Peroxidone K90 | PVP (and) Hydrogen Peroxide | 15.00 |
| Total | | 100.00 |

Whitening Composition of Example 3

| Trade Name | INCI Name | Weight (%) |
| --- | --- | --- |
| Ethanol | Alcohol | 61.35 |
| Propylene Glycol | Propylene Glycol | 15.00 |
| CP Carbamide Peroxide Cryst (Degussa/Evonik) | Urea Peroxide | 11.10 |
| Klucel HF Pharm (Hercules) | Hydroxypropylcellulose | 0.55 |
| Hercolyn D (Hercules) | Methyl Hydrogenated Rosinate | 12.00 |
| Total | | 100.00 |

A whitening composition in accordance with the invention may likewise include a surfactant to increase the ability of the solution to form cavitation bubbles. Such a surfactant may include zwitterionic and fluorinated surfactants. Particularly useful anionic surfactants include sodium lauryl sulfate, salts of dodecylbenzene sulfonate and sodium coconut monoglyceride sulfonates. A particularly useful nonionic surfactant is a water soluble polyoxyethylene monoester of sorbitol with a Cio-ig fatty acid ester of sorbitol (and sorbitol anhydrides), consisting predominantly of the monoester, condensed with about 10-30, preferably about 20, moles of ethyleneoxide. The fatty acid (aliphatic hydrocarbon-monocarboxylic acid) may be saturated or unsaturated, e.g. lauric, palmitic, stearic or oleic acids. Tween TM 20 is especially preferred, which is a poly-55 oxyethylene (20) sorbitan monolaurate. Capped polyalkylene oxide copolymer nonionic surfactants in which the hydrogens on the hydroxyl groups have been replaced with methyl groups are also useful in the present invention. For some known tooth whitening compositions, a thickener or thickening agent is added to increase the viscosity. The primary reason for this is to have the known whitening composition adhere to the teeth for a longer period of time. For most whitening compositions, the longer the time, the better the whitening result. Thickeners are also used for a system where the composition needs to be placed in a tray that is inverted for use with the bottom teeth.

In the present invention, a whitening composition with a thickener may be used in conjunction with sonochemistry, even though good results have been achieved without use of a thickener in the composition, such as set forth in the composition of Example 1 above. Other whitening compositions in accordance with the invention have included a thickener. Such thickeners may be used in an amount which provide for (i.e., do not hinder) the production of the desired cavitation bubbles to form. Thickeners such as neutralized carboxypolymethylene and other polyacrylic acid polymers and copolymers, hydroxypropylcellulose and other cellulose ethers, salts of poly(methyl vinyl ether-co-maleic anhydride), polyvinyl pyrrolidone (PVP), poly(vinylpyrrolidone-co-vinyl acetate), silicon dioxide, fumed silica, stearic acid esters, and others are found to have utility in the formulation of the oxidizing compositions and tooth whitening accelerator compositions.

In the case of the composition of Example 1 described herein, which included no thickeners, the liquid retaining element, such as the sponge or foam pad described above, for example, may be used in connection with the inventive method and device described herein, as will be readily appreciated.

Test results have shown that tooth whitening compositions according to the invention may be provided with thickener and be used for whitening teeth taking advantage of the benefits of sonochemistry as detailed herein.

Whitening systems that use light to heat known whitening compositions need to have non-opaque whitening compositions in order for the light to penetrate the composition. That is not a restriction in the present invention, although a clear composition would work just as well as an opaque composition in the inventive sonochemistry device and method described herein.

A whitening composition in accordance with the invention may include one or more flavorings in addition to or instead of the surfactant.

It is contemplated that any open celled sponge be used in accordance with the invention. The open cell structure (or foam for short) is needed so that the foam may be fully saturated with the whitening composition, such as a liquid whitening composition, which is necessary to efficiently transmit the ultrasound energy. Air bubbles in the pathway would act as small barriers to transmission and reduce the efficiency. Good results have been achieved with sponges of different materials and pore sizes. The sponge material should be chemically compatible with the whitening composition used, as will be readily appreciated. In accordance with the invention the sponges may be provided to the end user, such as the consumer, already saturated and individually packaged in a sealed container, such as a tray.

One example of a foam which may be used is a polyurethane foam, such as SAQ series Hydrophilic Polyurethane foam available from INOS Technologies, Ann Arbor, Mich. 48108 USA. It is contemplated that any open-celled foam may be used.

Data from Graph of FIG. 11.

| Time (min) | ΔE |
|---|---|
| Control Whitening Composition (Without light/heat) | |
| 2 | 4.75 |
| 4 | 5.39 |
| 6 | 5.96 |
| 8 | 6.37 |
| 10 | 6.87 |
| 20 | 8.15 |
| 30 | 8.41 |
| 40 | 9.68 |
| 50 | 10.53 |
| 60 | 11.47 |
| Control Whitening Composition (With light/heat) | |
| 2 | 4.05 |
| 4 | 6.31 |
| 6 | 6.40 |
| 8 | 7.05 |
| 10 | 7.6 |
| 20 | 10.59 |
| 30 | 13.31 |
| 40 | 14.59 |
| 50 | 15.77 |
| 60 | 17.24 |

Data from the Graph of FIG. 11 (cont.):

| Time (min) | ΔE |
|---|---|
| Control Whitening Composition (With Ultrasonic Whitening Device at a frequency of 40 kHz) | |
| 2 | 3.87 |
| 4 | 7.73 |
| 6 | 9.33 |
| 8 | 11.30 |
| 10 | 16.01 |

Data from additional testing of changes in delta E as a function of the frequency (kHz).

In the chart below, at Time=zero, delta E (ΔE)=zero (0); and the tested bovine teeth were naturally stained, so the changes in Delta E are less pronounced than the changes shown in the above charts, and in the graph of FIG. 11. No corresponding graph was provided, as this data shows the changes and improvements in the increase in delta E; i.e., the good results achieved with the whitening composition of Example 1 detailed above, and as set forth in the two (2) charts below:

| Time (min.) | Control - No Ultrasound (ΔE) | 22.5 kHz Probe (ΔE) | 42 kHz bath (ΔE) | 80 kHz bath (ΔE) |
|---|---|---|---|---|
| 0 | 0 | 0 | 0 | 0 |
| 5 | — | 1.35 | — | — |
| 20 | 0.20 | — | 1.67 | 0.91 |

In the chart below, at Time=zero, delta E (ΔE)=zero (0); and the tested bovine teeth were stained, so the changes in Delta E are more pronounced than the changes shown in the chart immediately above, in which the Whitening Composition of Example 1 above was likewise tested.

Effect of Ultrasound on
Whitening Composition of Example
1 (ΔE on stained bovine teeth)

| Time (minutes) | No Ultrasound | 40 kHz Ultrasound |
|---|---|---|
| 4 | 1.63 | 5.85 |
| 8 | 2.68 | 10.02 |
| 12 | 5.05 | 13.74 |
| 16 | 6.96 | 16.89 |
| 20 | 7.82 | 18.18 |

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A tooth whitening device for whitening teeth using sonochemistry, comprising:
    a) a body, the body having a female receptacle;
    b) an ultrasonic transducer provided in the body, the ultrasonic transducer being configured for producing ultrasonic waves of a sufficient frequency to induce a sonochemical reaction in a liquid tooth whitening composition, the sufficient frequency being a frequency of 20-100 kHz;
    c) an ultrasonic horn provided on the body, the ultrasonic horn including a male insert configured for being received in the female receptacle and connecting the ultrasonic horn to the body, and the ultrasonic horn being operatively connected with the ultrasonic transducer for transmitting ultrasonic waves into a liquid tooth whitening composition, the ultrasonic horn including an arch-shaped surface on a free end of the ultrasonic horn, and the ultrasonic horn being configured for transmitting the ultrasonic energy along the whole of the arch-shaped surface, the arch-shaped surface being substantially curved and configured for following a contour of a user's outer front teeth, the arch-shaped surface configured to face the user's outer front teeth, and the arch-shaped surface having a first free end and a spaced apart second free end;
    d) the ultrasonic transducer extending away from the ultrasonic horn, the ultrasonic transducer being configured for directing ultrasonic energy from the ultrasonic transducer toward the user's outer front teeth;
    e) a detachable liquid retaining element provided on the arch-shaped surface, the detachable liquid retaining element including a first sleeve configured for receiving the first free end of the arch-shaped surface of the ultrasonic horn, the detachable liquid retaining element including a second sleeve configured for receiving the second free end of the arch-shaped surface of the ultrasonic horn, and the detachable liquid retaining element having an arch-shaped inner surface so as to conform to the user's teeth; and
    f) the detachable liquid retaining element including an absorbent material and being configured for retaining a liquid tooth whitening composition against a user's teeth during a sonochemical reaction induced by ultrasonic waves transmitted into a liquid tooth whitening composition by the ultrasonic transducer moving the ultrasonic horn at a frequency of 20-100 kHz.

2. A tooth whitening device for whitening teeth using sonochemistry as in claim 1, wherein:
    a) the absorbent material includes a sponge.

3. A tooth whitening device for whitening teeth using sonochemistry as in claim 2, wherein:
    a) the sponge includes an open-cell sponge.

4. A tooth whitening device for whitening teeth using sonochemistry as in claim 1, wherein:
    a) a power supply for the ultrasonic transducer is provided in the body, an indicator light is provided in the body, and control circuitry is operatively connected to the power supply and to the indicator light for controlling operation thereof.

5. A tooth whitening device for whitening teeth using sonochemistry as in claim 1, wherein:
    a) the body is configured for being handheld during operation thereof.

6. A tooth whitening device for whitening teeth using sonochemistry as in claim 1, wherein:
    a) the ultrasonic horn, and the detachable liquid retaining element are configured to ensure that the liquid tooth whitening composition avoids contact with the gums and other mouth tissues to ensure the liquid tooth whitening composition avoids harming the gums and mouth tissues, and also avoids the killing of mouth flora.

7. A tooth whitening device for whitening teeth using sonochemistry as in claim 1, wherein:
    a) the ultrasonic horn configured for transmitting the ultrasonic energy from the ultrasonic transducer at frequency of 20-100 kHz toward the user's outer front teeth is moved about 0.015 mm, measured peak to peak.

8. A method for whitening teeth using sonochemistry, comprising:
    a) providing a tooth whitening device, the tooth whitening device, including:
        i) a body, the body having a female receptacle;
        ii) an ultrasonic transducer provided in the body, the ultrasonic transducer being configured for producing ultrasonic waves of a sufficient frequency to induce a sonochemical reaction in a liquid tooth whitening composition, the sufficient frequency being a frequency of 20-100 kHz;
        iii) an ultrasonic horn provided on the body, the ultrasonic horn including a male insert configured for being received in the female receptacle and connecting the ultrasonic horn to the body, and the ultrasonic horn being operatively connected with the ultrasonic transducer for transmitting ultrasonic waves into a liquid tooth whitening composition, the ultrasonic horn including an arch-shaped surface on a free end of the ultrasonic horn, and the ultrasonic horn being configured for transmitting the ultrasonic energy along the whole of the arch-shaped surface, the arch-shaped surface being substantially curved and configured for following a contour of a user's outer front teeth, and the arch-shaped surface configured to face the user's outer front teeth, and the arch-shaped surface having a first free end and a spaced apart second free end;

iv) the ultrasonic transducer extending away from the ultrasonic horn, the ultrasonic transducer being configured for directing ultrasonic energy from the ultrasonic transducer toward the user's outer front teeth; and v) a detachable liquid retaining element provided on the arch-shaped surface, the detachable liquid retaining element including a first sleeve configured for receiving the first free end of the arch-shaped surface of the ultrasonic horn, the detachable liquid retaining element including a second sleeve configured for receiving the second free end of the arch-shaped surface of the ultrasonic horn, the detachable liquid retaining element having an arch-shaped inner surface so as to conform to the user's teeth, and the detachable liquid retaining element being configured for retaining a liquid tooth whitening composition against a user's teeth during a sonochemical reaction induced by ultrasonic waves;

b) providing a liquid tooth whitening composition on the detachable liquid retaining element;

c) causing the ultrasonic horn to be vibrated at an ultrasonic frequency of 20-100 kHz to induce a sonochemical reaction in a liquid tooth whitening composition; and d) holding the liquid tooth whitening composition on the detachable liquid retaining element adjacent the user's teeth for a predetermined period of time.

9. A method for whitening teeth using sonochemistry as in claim 8, wherein:

a) in the step of causing the ultrasonic horn to vibrate at an ultrasonic frequency of 20-100 kHz to induce a sonochemical reaction in a liquid tooth whitening composition, the ultrasonic horn is moved about 0.015 mm, measured peak to peak.

10. A method for whitening teeth using sonochemistry as in claim 8, wherein:

a) the ultrasonic horn is vibrated at an ultrasonic frequency of about 40 kHz.

11. A method for whitening teeth using sonochemistry as in claim 8, wherein:

a) the liquid tooth whitening composition includes an oxidizing agent.

12. A method for whitening teeth using sonochemistry as in claim 11, wherein:

a) the oxidizing agent includes hydrogen peroxide.

13. A method for whitening teeth using sonochemistry as in claim 12, wherein:

a) the hydrogen peroxide is provided in a percentage of 0.01-35.0%.

14. A method for whitening teeth using sonochemistry as in claim 11, wherein:

a) the oxidizing agent includes carbamide peroxide.

15. A method for whitening teeth using sonochemistry as in claim 14, wherein:

a) the carbamide peroxide is provided in a percentage of 0.01-35.0%.

16. A tooth whitening device for whitening teeth using sonochemistry, comprising:

a) a body;

b) an ultrasonic transducer provided in the body, the ultrasonic transducer being configured for producing ultrasonic waves of a sufficient frequency to induce a sonochemical reaction in a liquid tooth whitening composition, the sufficient frequency being a frequency of 20-100 kHz;

c) an ultrasonic horn provided on the body, the ultrasonic horn being operatively connected with the ultrasonic transducer for transmitting ultrasonic waves into a liquid tooth whitening composition, the ultrasonic horn including an arch-shaped surface on a free end of the ultrasonic horn, and the ultrasonic horn being configured for transmitting the ultrasonic energy along the whole of the arch-shaped surface, the arch-shaped surface being substantially curved and configured for following a contour of a user's outer front teeth, the arch-shaped surface configured to face the user's outer front teeth, surface facing toward the the arch-shaped surface having a first free end and a spaced apart second free end, and the ultrasonic horn is configured for movement of about 0.015 mm, measured peak to peak;

d) the ultrasonic transducer extending away from the ultrasonic horn, the ultrasonic transducer being configured for directing ultrasonic energy from the ultrasonic transducer toward the user's outer front teeth;

e) a detachable liquid retaining element provided on the arch-shaped surface, the detachable liquid retaining element including a first sleeve configured for receiving the first free end of the arch-shaped surface of the ultrasonic horn, the detachable liquid retaining element including a second sleeve configured for receiving the second free end of the arch shaped surface of the ultrasonic horn, the detachable liquid retaining element having an arch-shaped inner surface so as to conform to the user's teeth; and f) the detachable liquid retaining element including an absorbent material and being configured for retaining a liquid tooth whitening composition against a user's teeth during a sonochemical reaction induced by ultrasonic waves transmitted into the liquid tooth whitening composition by the ultrasonic transducer moving the ultrasonic horn at a frequency of 20-100 kHz.

17. A tooth whitening device for whitening teeth using sonochemistry as in claim 16, wherein:

a) the ultrasonic horn is configured for transmitting the ultrasonic energy along the whole of the arch-shaped surface.

* * * * *